US009713518B2

(12) United States Patent
Adams et al.

(10) Patent No.: US 9,713,518 B2
(45) Date of Patent: Jul. 25, 2017

(54) SACROCOLOPOPEXY IMPLANTS AND RELATED METHODS OF USE (71) Applicant: Boston Scientific Scimed, Inc., Maple Grove, MN (US)

(72) Inventors: Kenneth W. Adams, Wilmington, MA (US); David L. Mason, Marlborough, MA (US); James M. Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 72 days.

(21) Appl. No.: 14/563,528

(22) Filed: Dec. 8, 2014

(65) Prior Publication Data

US 2015/0157438 A1 Jun. 11, 2015

Related U.S. Application Data (60) Provisional application No. 61/913,636, filed on Dec. 9, 2013.

(51) Int. Cl.
*A61F 13/00* (2006.01)
*A61F 2/00* (2006.01)

(52) U.S. Cl.
CPC .................. *A61F 2/0045* (2013.01)

(58) Field of Classification Search
CPC .... A61F 2/0004; A61F 2/0031; A61F 2/0036; A61F 2/0045; A61F 2/0063; A61B 17/0401; A61B 17/06109
USPC .......... 600/29–32, 37; 128/DIG. 25
See application file for complete search history.

(56) References Cited

U.S. PATENT DOCUMENTS

| 8,663,086 B2* | 3/2014 | Duncan ................. A61F 2/0036 600/30 |
| 9,017,243 B2* | 4/2015 | Roll .................... A61B 17/0401 600/37 |
| 2006/0089525 A1* | 4/2006 | Mamo ................ A61B 17/0401 600/37 |
| 2009/0259094 A1 | 10/2009 | Bouchier et al. |
| 2010/0174134 A1 | 7/2010 | Anderson et al. |
| 2010/0261950 A1 | 10/2010 | Lund et al. |
| 2010/0312052 A1 | 12/2010 | Morningstar et al. |
| 2010/0331612 A1 | 12/2010 | Lashinski et al. |
| 2011/0112357 A1* | 5/2011 | Chapman .......... A61B 17/0401 600/37 |
| 2015/0157440 A1 | 6/2015 | Flynn et al. |

\* cited by examiner

*Primary Examiner* — John Lacyk
(74) *Attorney, Agent, or Firm* — Brake Hughes Bellermann LLP (57) ABSTRACT Some embodiments are directed to implants and methods for making and using the implants. An exemplary implant includes a first elongate member and a second elongate member each having a first end portion and a second end portion. The first and second end portions of the first elongate member may be configured to be coupled to tissue of a patient proximate the vagina and sacrum, respectively. The first elongate member may define a first opening and a second opening, where the second elongate member may be configured to extend through the first opening and the second opening. The first end portion of the second elongate member may be coupled to tissue proximate the vagina of the patient.

12 Claims, 7 Drawing Sheets

SACROCOLOPOPEXY IMPLANTS AND RELATED METHODS OF USE

CROSS-REFERENCE TO RELATED APPLICATION

This application is a Nonprovisional of, and claims priority to, U.S. Patent Application No. 61/913,636, filed on Dec. 9, 2013, entitled "SACROCOLOPOPEXY IMPLANTS AND RELATED METHODS OF USE", which is incorporated by reference herein in its entirety.

TECHNICAL FIELD

The disclosed invention relates generally to medical devices, implants, and methods for delivering implants within a pelvic region of a patient to treat various pelvic dysfunctions. More particularly, the disclosed invention relates to sacrocolopopexy implants to treat prolapse of pelvic organs.

BACKGROUND

A variety of medical procedures are performed to treat various female pelvic dysfunctions, including procedures to treat urinary incontinence, and correcting various pelvic organ prolapse (POP) conditions, such as, uterine prolapse, cystoceles, rectoceles, and vaginal vault prolapse. A cystoceles occurs when the bladder bulges into the vagina; a rectocele occurs when the rectum bulges into the vagina; a hysterocele occurs when the uterus descends into the vagina; and an enterocele (small bowel prolapse) occurs when the small bowel pushes through the upper wall of the vagina.

The existing procedures for treating POP usually include implanting pelvic implants within a variety of different anatomical structures within a pelvic region. For example, some sacrocolopopexy procedures involve delivering and securing a mesh to support the vagina by affixing it at one end portion to tissue near the sacrum of the patient and affixing it at another end portion to tissue proximate the vagina of the patient. Physicians may purchase rectangular mesh sheets from which they cut shapes as per their objectives for the procedure. A Y-shaped mesh implant may also be used for treating POP, which may reduce the time required to cut and assemble mesh during the procedure. However, some physicians may still continue to buy mesh sheets to create their own implants because it gives them flexibility to separately position and adjust two mesh pieces, which may be a limitation with conventional Y-shaped meshes.

Therefore, there exists a need for implants that may be implanted in the body of the patient without lengthy customizing and thus, avoiding consumption of extra time and efforts.

SUMMARY

The present disclosure provides alternative implants as well as methods for manufacturing and using the alternative implants that addresses one or more of the above mentioned issues.

One illustrative embodiment discloses an implant having a first elongate member and a second elongate member. The first elongate member has a first end portion and a second end portion, the former is configured to be coupled to tissue proximate a vagina of a patient and the latter is configured to be coupled to tissue proximate a sacrum of the patient. The first elongate member defines a first opening and a second opening. Further, the second elongate member has a first end portion and a second end portion such that the former is coupled to tissue proximate the vagina of the patient. The second elongate member is configured to extend through the first opening and the second opening of the first elongate member.

Another illustrative embodiment discloses an implant having a first elongate member and a second elongate member. The first elongate member has a first end portion and a second end portion such that the former is configured to be coupled to tissue proximate a vagina of a patient and the latter is configured to be coupled to tissue proximate a sacrum of the patient. The first elongate member defines an opening. Further, the second elongate member has a first end portion and a second end portion such that the former is coupled to tissue proximate the vagina of the patient and the latter is configured to be coupled to tissue proximate a sacrum of the patient. The second elongate member is configured to extend through the opening of the first elongate member.

Another illustrative embodiment discloses an implant having a first elongate member and a second elongate member each having a first end portion and a second end portion. The first elongate member includes a coupling tab having the second end portion of the second elongate member attached thereto. The first end portions of the first and second elongate members are configured to be coupled to tissue proximate a vagina of a patient.

Another illustrative embodiment of the present disclosure discloses a method of placing an implant, where the implant has a first elongate member and a second elongate member. The method includes coupling a first end portion of the elongate member of the implant to tissue proximate a first portion of a vagina of a patient and coupling the second end portion of the first elongate member of the implant to tissue proximate a sacrum of the patient. The method further includes passing the second elongate member through an opening defined by the first elongate member.

Yet another illustrative embodiment of the present disclosure discloses a method of placing an implant, where the implant has a first elongate member and a second elongate member. The method includes coupling a first end portion of the first elongate member of the implant to tissue proximate a first portion of a vagina of a patient and coupling a second end portion of the first elongate member of the implant to tissue proximate a sacrum of the patient. The method further includes coupling a first end portion of the second elongate member to the first elongate member and adjusting a suture loop to move the first elongate member with respect to the second elongate member.

The above summary of some embodiments is not intended to describe each disclosed embodiment or every implementation of the present disclosure. The Figures, and Detailed Description, which follow, more particularly exemplify these embodiments, but are also intended to be exemplary and not limiting.

BRIEF DESCRIPTION OF THE DRAWINGS

The disclosure may be more completely understood in consideration of the following detailed description of various embodiments in connection with the accompanying drawings.

DETAILED DESCRIPTION

Definitions of certain terms are provided below and shall be applied, unless a different definition is given in the claims or elsewhere in this specification.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings, in which similar elements in different drawings are identified with the same reference numbers. The drawings, which are not necessarily to scale, depict illustrative embodiments and are not intended to limit the scope of the disclosure.

The devices and methods described herein are generally directed to implants and the delivery and placement of such implants within a pelvic region (also referred to herein as "pelvis") of a patient. In other embodiments, the devices and methods may be used to place implants in other locations within the body of the patient.

Various embodiments of implants are described herein. An implant can be delivered to a pelvic region of a patient using a variety of different delivery devices, only some examples of which are described herein.

Figure 1:
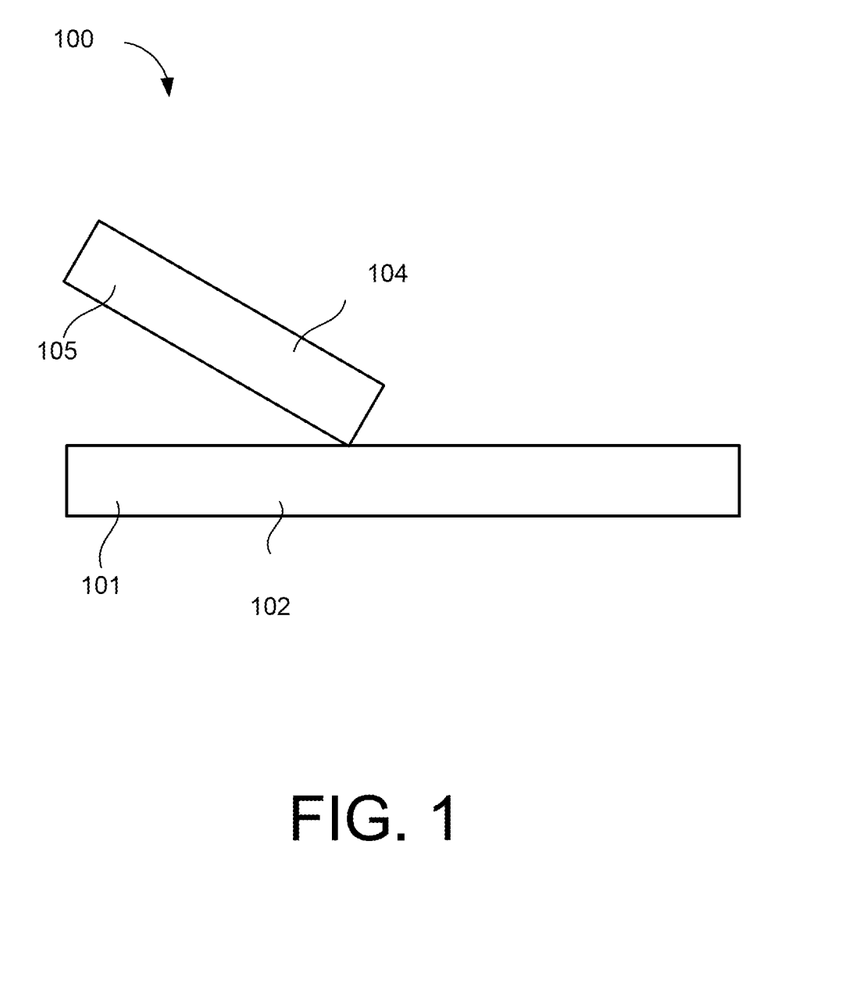
FIG. 1 is a schematic illustration of an implant, according to an embodiment of the invention.

FIG. 1 is a schematic illustration of an implant 100, according to an embodiment of the present disclosure. The implant 100 is configured to be placed within a body of a patient and provide support to the body or a portion of the body of the patient. In some embodiments, the implant 100 provides support to one or more pelvic organs in case of pelvic organ prolapse. For example, the implant 100 may be used to provide support to the vagina of the patient to treat vaginal vault prolapse. Similarly, the implant 100 may be employed to provide support to other body portions such as rectum, bladder, abdomen, or the like.

The implant 100 includes a first elongate member 102 and a second elongate member 104 such that the two elongate members 102, 104 may be coupled together. The two elongate members 102, 104 may couple to roughly form a Y-shaped configuration. This implant 100 may be configured to couple the vagina, for example the vaginal apex, of a patient to tissue near the sacrum or tail bone of the patient. Any suitable structures or devices may be used to couple the implant to the vaginal and sacral tissues. Examples of such structures of devices may include sutures, pins, tacks, staples, glues, adhesives, or the like. Such structures or devices may be discussed in more detail in conjunction with FIG. 6.

In an embodiment, the first elongate member 102 of the implant 100 couples to a posterior wall of the vagina (or tissue proximate such wall), whereas the second elongate member 104 couples to an anterior wall of the vagina (or tissue proximate such wall). In particular, a first end portion 101 of the first elongate member 102 couples to the posterior wall of the vagina and a first end portion 105 of the second elongate member 104 couples to the anterior wall of the vagina. In other embodiments, the first elongate member 102 may be coupled to the anterior wall of the vagina and the second elongate member 104 may be coupled to the posterior wall of the vagina. The term "posterior wall" is used herein to mean an area in the pelvic region located on the backside of the vagina or towards the rear of the vaginal apex of the patient, whereas the term "anterior wall" is used to mean an area in the pelvic region located in the front side of the vagina or towards the front of the vaginal apex of the patient.

The first elongate member 102 and the second elongate member 104 may be tensioned independently prior to being coupled together. This may allow an efficient real-time in-vivo tensioning of the implant 100 to match the patient's anatomy, which may be helpful for providing adequate support to the vagina. In this way, the physician does not have to make pre-operative examinations to make determinations regarding the patient's anatomy and customize available implant material accordingly. As a result, irregular cuts on the implant material (such as a mesh), which may compromise its mechanical integrity, may be avoided. A physician's ability to independently tension the elongate members may allow for greater customization to meet the needs of the patient with sufficient mechanical support.

In some embodiments, a coupling mechanism may be employed to attach the first and second elongate members 102, 104 to the body tissue. Exemplary coupling mechanisms may include sutures, staples, pins, glues, adhesives, and so forth. A similar coupling means (a suture or other coupling means) may be employed to removably couple the first elongate member 102 to the second elongate member 104, which can produce a desired tension in the elongate members 102, 104 while connecting the implant 100 to the vagina and the sacrum. In some embodiments, the first elongate member 102 is frictionally coupled to the second elongate member 104. Such coupling mechanisms will be discussed in detail in conjunction with FIG. 6 below.

Materials employed to manufacture the implant 100 may include any suitable biocompatible material. In some embodiments, the material has sufficient flexibility so that the implant can extend between the vaginal and sacrum regions of the patient's body. In addition, it may have enough strength to withstand tension applied during the procedure and provide sufficient support to the vagina. Such materials may include, but are not limited to, polymers, such as, polyester, silk, nylon, polydioxinone, polygylcolic acid, etc.; and natural grafts, such as, porcine dermis, small intestinal submucosa, etc. In some embodiments, the implant 100 may be formed as a mesh, which may be made from either a monofilament or multifilament macroporous polypropylene.

In some embodiments, the implant 100 may be formed with flexible portions, rigid portions, or both. For example, the implant 100 may be formed of a mesh material that includes a tight weave or a loose weave pattern. Additionally, the mesh material may include many small apertures or may include a few larger apertures. In some embodiments, one portion of the implant 100 may be more elastic than another portion of the implant 100. For example, in some embodiments, the portions of the implant 100 that are configured to be coupled to or proximate to the vagina of the patient may be more elastic than other portions of the implant (such as the portion configured to be coupled to or proximate the sacrum). In some embodiments, the implant 100 may include reinforcement portions that are configured to provide structures or rigidity to portions of the implant 100. In some embodiments, the implant 100 may be configured to flex or stretch more in one direction (or along one axis) than in a second direction (or along a second axis).

In some embodiments, the implant 100 is formed of a biodegradable portion and a non-biodegradable portion. For example, in some embodiments, the implant 100 is formed of a woven material. Some or at least one of the fibers forming the woven material may be at least partially formed of a biodegradable material.

Figure 2:
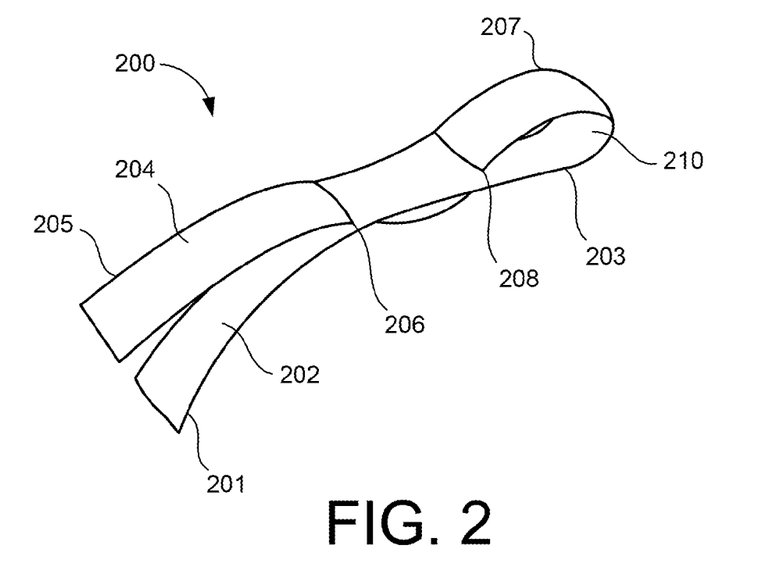
FIGS. 2 and 3 are perspective views of two implants, according to embodiments of the invention.

Turning now to FIG. 2, a perspective view of an implant 200 is illustrated. The implant 200 includes a first elongate member 202 and a second elongate member 204. The implant 200 is configured to be placed within a body of a patient and provide support to the body or a portion of the body of the patient. For example, the implant 200 may be used to provide support to the vagina of the patient in case of vaginal vault prolapse.

The first elongate member has a first end portion 201 and a second end portion 203 such that the first end portion 201 may couple to a portion, such as a posterior portion of the vaginal wall (or tissue proximate such wall), and the second end portion 203 coupled to a sacrum tissue or tissue proximate the sacrum of the patient. The second elongate member 204 also has a first end portion 205 and second end portion 207 such that the former couples to a portion of the vagina, such as an anterior portion of the vaginal wall, and the latter couples to the sacrum tissue or tissue proximate the sacrum of the patient.

According to an embodiment, the implant 200 is a single or unitary structure, in which the first and second elongate members 202, 204 are formed from one piece of material into a Y-shaped implant 200. In this embodiment, the first end portions 201 and 205 of the two elongate members 202 and 204 couples to the anterior and posterior vaginal walls (or tissue proximate such walls), respectively, whereas the second end portions end portions 203 and 205 may be coupled together and/or to a common site proximate the sacrum tissue. Alternatively, the first and second elongate members 202, 204 may be separate pieces of material that are linked together to one another defining a partially X-shaped configuration. In such an instance, the second end portion 203 of the first elongate member 202 may couple to a first tissue portion of the sacrum, whereas the second end portion 207 of the second elongate member 204 may couple to a second tissue portion of the sacrum of the patient.

As shown in FIG. 2, the first elongate member 202 includes a first opening 206 and a second opening 208 such that the two openings 206, 208 are disposed along a surface of the first elongate member 202 between the first end portion 201 and the second end portion 203. The second elongate member 204 is configured to extend through the first and second openings 206, 208 of the first elongate member 202, thus forming a loop portion 210. In an alternate embodiment, the location of the opening 206 and 208 may be towards the edge or side portions of the first elongate member 202 instead of in the middle section so as to maintain the mechanical integrity of the mesh material of the implant 200. In some embodiments, the first elongate member 202 may include a single opening such that the second elongate member 204 can be fed through the opening to form a loop-shaped structure.

In some embodiments, rather than an opening or openings, the first elongate member 202 defines a slit or a slot that extends to an edge portion of the first elongate member 202. Accordingly, the second elongate member 204 may be disposed within such slit or slot.

In addition, the implant 200 is illustrated with two openings 206, 208 in the first elongate member 202, however, it is contemplated that either of the first or second elongate members 202, 204 may have any suitable number of openings including one, three, four, and so forth, to accomplish the desired purpose. In some other embodiments, the first and second elongate members 202, 204 may both have one or more such openings.

The first elongate member 202 may be made from a mesh material such as polypropylene, or the like. In these embodiments, the strength and integrity of the mesh may be dictated by dimension and structure of the mesh. For instance, the mesh material includes multiple fibers weaved to define interstices. It should be noted that the dimensions of the pore size of such interstices should be smaller than the dimensions of the first and second openings 206, 208. In some embodiments, the second elongate member 204 may also be made from the mesh material having a pore size with dimensions smaller than that of the first and second openings 206, 208.

Other suitable materials employed to manufacture the implant 200 may include any suitable biocompatible material. In some embodiments, the material has sufficient flexibility so that the implant can extend between the vaginal and sacrum regions of the patient's body. In addition, it may have enough strength to withstand tension applied during the procedure and provide sufficient support to the vagina. Such materials may include, but are not limited to, polymers, such as, polyester, silk, nylon, polydioxinone, polygylcolic acid, etc.; and natural grafts, such as, porcine dermis, small intestinal submucosa, etc.

In some embodiments, the implant 200 may be configured to be coupled within the openings. For example, in some embodiments, the implant 200 may be configured to frictionally fit or couple within the opening or openings. In some embodiments, the implant 200 may include ridges or rough edges to help facilitate the coupling of the implant within the opening or openings.

Figure 3:
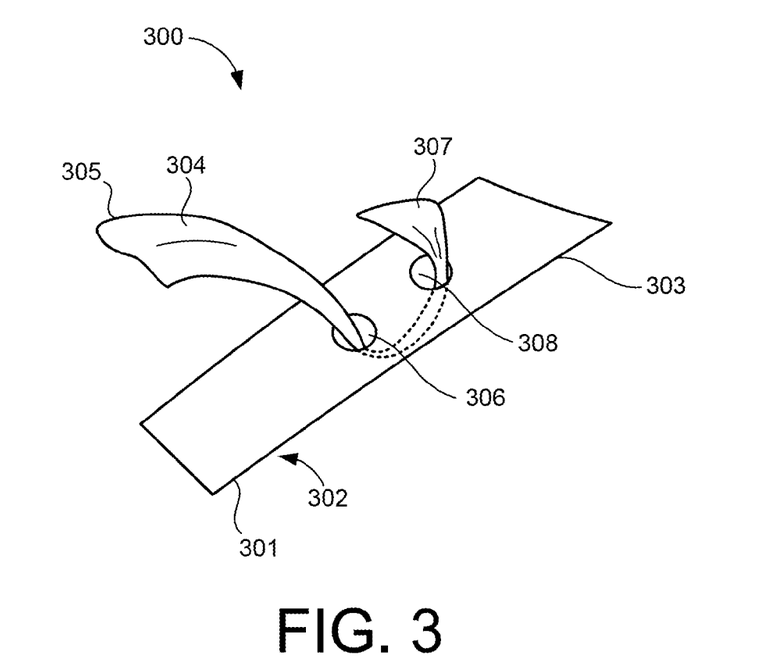

FIG. 3 is a perspective view of an implant 300 according to another embodiment. As shown, the implant 300 includes a first elongate member 302 and a second elongate member 304. The implant 300 may have similar functionality and application as that of the implant 200 shown in FIG. 2.

In contrast to the implant 200 of FIG. 2, in the present embodiment, the first elongate member 302 may be longer than the second elongate member 304 so that the first elongate member 302 can connect or extend from the vagina wall to the sacrum or tissue proximate the sacrum of the patient. In particular, the longer first elongate member 302 may be coupled to the anterior wall or posterior wall (or tissue proximate such walls) of vagina at its first end portion 301 and to the sacrum or tissue proximate the sacrum at a second end portion 303, whereas the second elongate member 304 may couple to the other of the posterior wall and anterior wall of the vagina (or tissue proximate such walls) at its first end portion 305 such that a second end portion 307 may couple to a middle portion of the first elongate member 302. In such a manner, the first elongate member 302 may provide support to posterior wall of the vagina, while the second elongate member 304 may provide support to anterior wall of the vagina.

The first elongate member 302 defines a first opening 306 and a second opening 308 disposed along a surface of the first elongate member 202. The two openings 306, 308 are disposed between the first end portion 301 and the second end portion 303. The second elongate member 304 is configured to extend through the first and second openings 306, 308 of the first elongate member 302. In some embodiments, the second elongate member 304 is frictionally coupled to the first elongate member 302, while extending through the two openings 306 and 308. In some other embodiments, the first elongate member 302 may be coupled to the second elongate member 304 after the tension has been set. The coupling may be done by sewing the first elongate member 302 to the second elongate member 304 or using other suitable coupling means such as gluing, stapling, or the like.

Although the implant 300 defines two openings 306, 308 in the first elongate member 302, it should be contemplated that either of the first or second elongate members 302, 304 may have any suitable number of openings including one, three, four, and so forth, to accomplish the desired purpose. In some other embodiments, the first and second elongate members 302, 304 may both have one or more such openings.

In some embodiments, the first elongate member 302 is made from a mesh material such as polypropylene, or the like. In such embodiments, the strength and integrity of the mesh may be dictated by dimension of the mesh. For instance, the mesh material includes multiple fibers interweaved to define interstices. It should be noted that the dimensions of the pore size of such interstices should be smaller than the dimensions of the first and second openings 306, 308.

In some embodiments, the second elongate member 304 may also be made from the mesh material having a pore size with dimensions smaller than that of the first and second openings 306, 308.

Other suitable materials employed to manufacture the implant 300 may include any suitable biocompatible material, as described with respect to implant 200.

Figure 4:
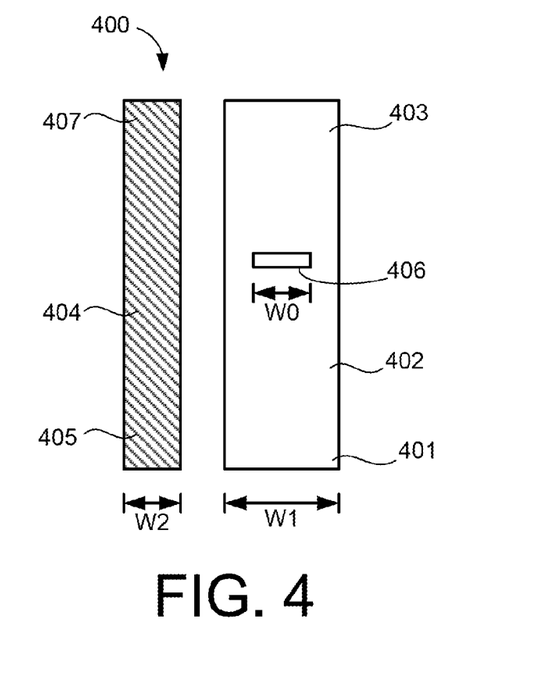
FIG. 4 is a top view of an implant prior to assembly, according to an embodiment of the invention.

FIG. 4 is a top view of an implant 400, according to an embodiment. The implant 400 includes a first elongate member 402 having a first end portion 401 and a second end portion 403, and a second elongate member 404 having a first end portion 405 and a second end portion 407. The implant 400 may have a similar structure and function as that of implants 200 and 300 of FIGS. 2 and 3, respectively.

The first end portion 401 of the first elongate member 402 may be coupled to tissue proximate the vagina of a patient and its second end portion 403 is configured to be coupled to tissue proximate a sacrum of the patient. Similarly, the first end portion 405 of the second elongate member 404 is configured to be coupled to tissue proximate the vagina of the patient and the second end portion 407 of the second elongate member 404 is configured to be coupled to tissue proximate the sacrum of the patient. In particular, the first end portion 401 of the first elongate member 402 may couple to a portion of a vagina, such as a posterior portion of the vagina or other tissue proximate the vagina, of the patient, whereas the first end portion 405 of the second elongate member 404 may couple to a portion of the vagina, such as an anterior portion of the vagina or other tissue proximate the vagina, of the patient.

The first elongate member 402 defines an opening 406 disposed along a surface of the elongate member 402. The second elongate member 404 is configured to extend through the opening 406 such that the implant 400 may take on a substantially X-shaped configuration. The dimensions of the opening 406 should be such as to allow the second elongate member 404 to pass through, while maintaining the integrity and/or strength of the first elongate member 402. To this end, the width W0 of the opening 406 should be such as to allow the second elongate member 404 to pass therethrough. In such embodiments, the width W1 of the first elongate member 402 is greater than the width W2 of the second elongate member 404.

As shown, the opening 406 may be disposed at a midway portion of the first elongate member 402. The opening 406, however, may be made at any suitable position along the length of the first elongate member 402. In addition, any suitable number of openings may be made on either the first and/or the second elongate members 402, 404.

Figure 5:
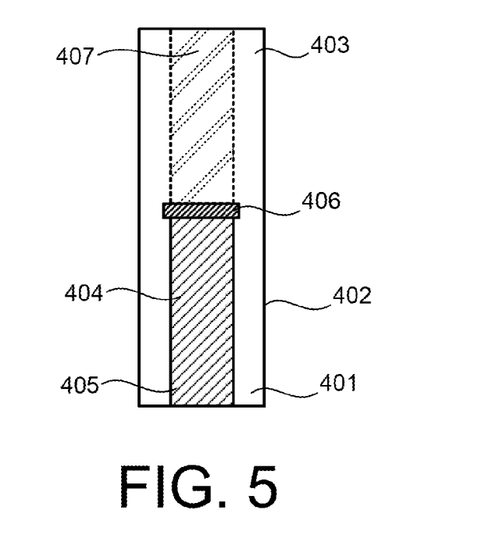
FIG. 5 is a top view of the implant of FIG. 4 after assembly.

FIG. 5 shows an assembled top view of the implant 400 of FIG. 4. As illustrated, the second elongate member 404 may extend through the opening 406 of the first elongate member 402. The implant 400 may be introduced inside the patient's body in this assembled configuration.

In the embodiment shown in FIGS. 4-5, the first elongate member 402 is made from a mesh material such as polypropylene, or the like. In such an embodiment, the strength and integrity of the mesh may be dictated by dimension of the mesh. For instance, the mesh material includes multiple fibers interweaved to define a pore size. It should be noted that the dimensions of the pore size of the mesh should be smaller than the dimensions (i.e. width W0) of the opening 406.

In some embodiments, the second elongate member 404 may also be made from the mesh material having a pore size with dimensions smaller than that of the opening 406.

Other suitable materials employed to manufacture the implant 400 may include any suitable biocompatible material, as described with respect to implants 200 and 300.

Figures 6, 7, 8:
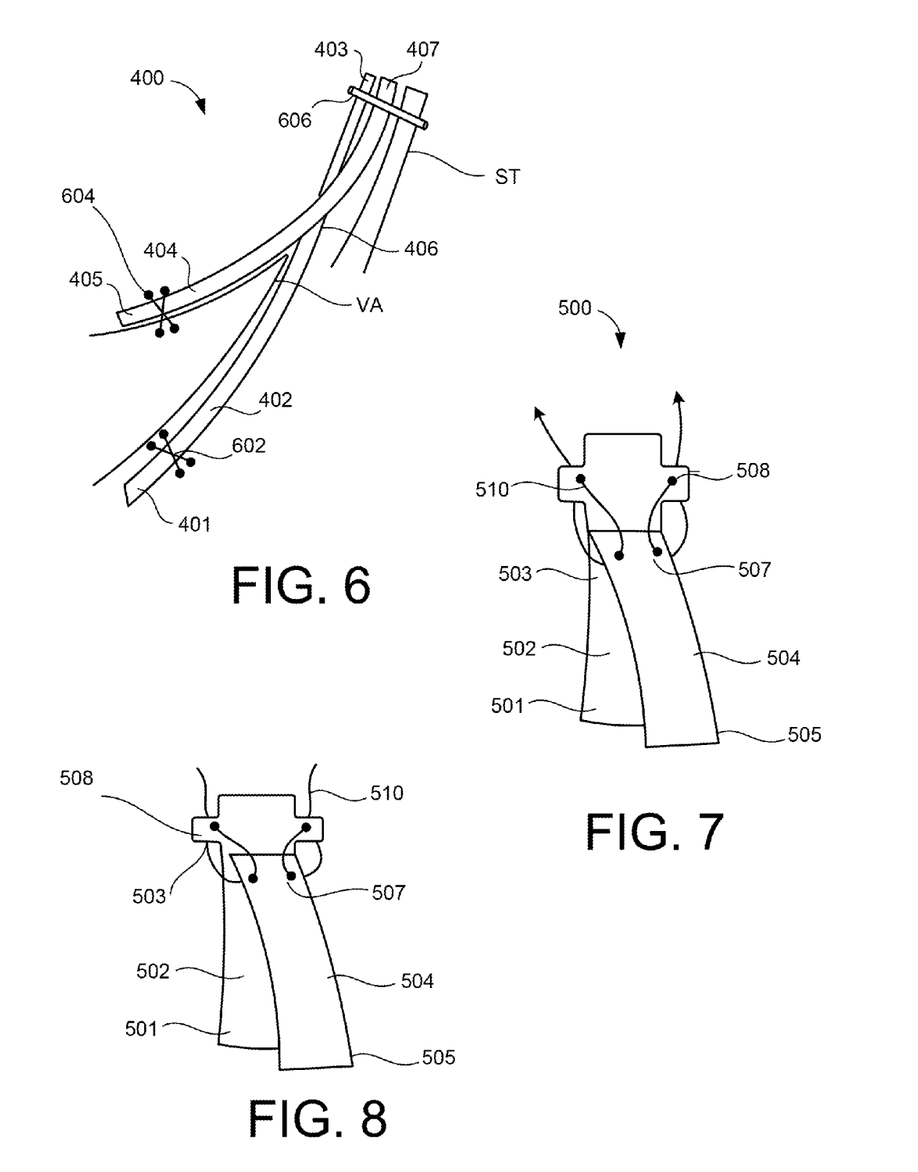
FIG. 6 is a schematic illustration of the implant of FIG. 4 disposed within a body of a patient.
FIGS. 7 and 8 are perspective views of an implant, according to an embodiment of the invention.

FIG. 6 is a schematic illustration of the implant 400 after it has been placed within the body of a patient. The implant 400 can be implanted using any suitable surgical or non-surgical technique known in the art. In some embodiments, the implant 400 is placed within the body of the patient using a minimally-invasive delivery device. For instance, a laparoscope may be used to transport the implant to the treatment location near the vagina, for example the vaginal apex. In alternate embodiments, the implant may be placed within the body of the patient transvaginally i.e., by making the vaginal incision.

For example, in one embodiment, the implant 400 is placed or implanted within the body of a patient through an incision at a suitable location such as on or proximate to an anterior wall of the vagina. Alternatively, the implant 400 is placed within the patient's body through an abdominal incision. In either of the procedures, once the incision is made, the physician may insert the implant 400 into the body of the patient through the incision using an insertion device with a handle. In an approach, the second end portions 403 and 405 of the first and second elongate members 402 and 404 may be coupled to or proximate to the sacrum tissue ST of the patient, which may be followed by a positioning of the first end portions 401 and 405 of the two elongate members 402 and 404 within the body of the patient such that the first end portions 401 and 405 are disposed adjacent or proximate the vaginal apex VA of the patient. In particular, the first end portion of the first elongate member 402 may be positioned and coupled adjacent the posterior portion of the of the patient's vagina, whereas the first end portion 405 of the second elongate member 404 may be coupled to the anterior portion of the vaginal apex of the patient.

In some embodiments, the first end portions 401 and 405 and the second end portions 403 and 407 are stitched or sewn to the vaginal apex (or tissue proximate the vaginal apex) and the sacrum tissue of the patient, respectively, using sutures or the like. In some embodiments, the coupling may removably couple the elongate members (402 and 404) to tissue so that it can be attached and detached, as needed. The implant 400 may be coupled using other couplers such as tacks to engage the second end portions 403 and 407 of the implant 400 to the sacrum wall of the patient's body. For example, the coupling may include a tapered nail or pin portion for piercing tissue and a head portion for user manipulation. Any suitable coupling mechanism such as, but not limited to, staples, pins, anchors, glues, adhesives, or the like may be employed to couple the implant 400 within the patient's body. In other embodiments, the implant 400 may include structures like barbs, dimples and/or other protrusions configured to engage the bodily tissue of the patient to help retain the implant 100 in place within the body of the patient.

An embodiment of the implant with coupling tabs is shown in FIGS. 7 and 8, according to another embodiment of the invention. The implant 500 includes a first elongate member 502 and a second elongate member 504. The implant 500 may have a similar structure and function as that of the implants 200, 300, and 400 of FIGS. 2-6.

The first elongate member 502 has a first end portion 501 and a second end portion 503, where the former is configured to be coupled to tissue proximate the vagina of a patient. Similarly, the second elongate member 504 has a first end portion 505 and a second end portion 507 such that the former is configured to be coupled to a tissue proximate the vagina of the patient.

As shown, the first elongate member 502 further includes a coupling mechanism, specifically coupling tabs 508 extending from a side portion 509 of the first elongate member 502. The coupling tabs 508 may be disposed at any location along the length of the first elongate member 502. The second end portion 507 of the second elongate member 504 is configured to be coupled to the coupling tab 508 of the first elongate member 502 using a coupler such as a suture 510. Other couplers such as screws, pins, staples, glues, adhesives, or the like may also be used for the desired purposes. To accomplish this, the suture 510 may be pulled in a direction D to independently tension the second elongate member 504 as shown in FIG. 8. The operator may also apply tension to the first elongate member 502 by pulling on the second end portion 503 of the member 502. The implant 500 may be coupled to or proximate to the sacrum tissue of the patient's body using other coupling means (not shown) to maintain the desired tension.

According to an example, the first elongate member 502 may be coupled to the vaginal wall (or tissue adjacent such wall) at one end and the sacrum at another end. Then, the second elongate member 504 may be coupled to or proximate to the vaginal wall. The second elongate member 504 may then be tensioned with the suture 510, which may employs structures such as knots, locks, or the like to lock the member 504 upon pulling.

Although a single coupling tab 508 is employed, it should be contemplated that any suitable number of coupling tabs such as two, three, and so forth may be employed for the desired purposes. In an embodiment, the implant 500 includes two coupling tabs such that a first coupling tab may be configured to be coupled to the first elongate member 502 and a second coupling tab may be coupled to the second elongate member 504.

Materials employed to manufacture the implant 500 may include any suitable biocompatible material including, yet not limited to, metals, polymers, alloys, or the like, as described above for implants 200, 300, and 400.

Figure 9:
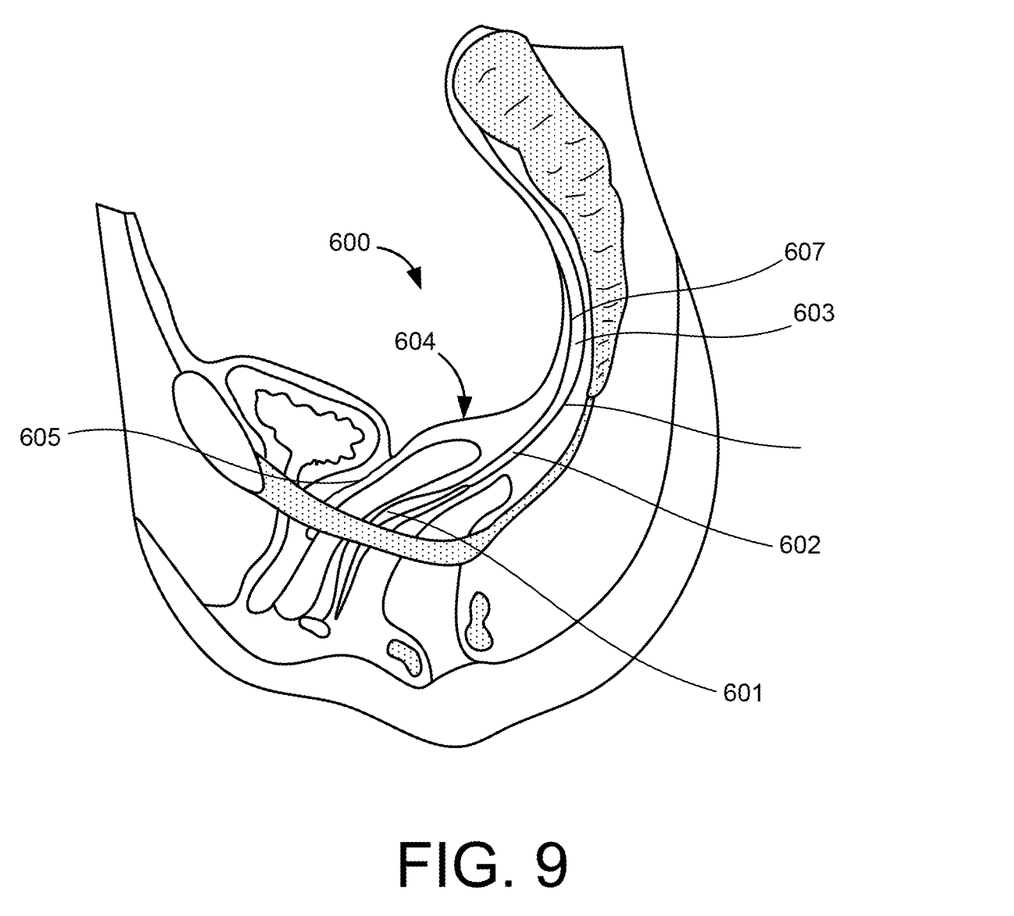
FIG. 9 is a schematic illustration of an implant, according to an embodiment of the invention disposed within a body of a patient.

After implantation, implants 600 may be disposed within a body of a patient, as shown in FIG. 9. The implant 600 may be partially disposed on the posterior side and the anterior side of the body to support the vagina by attaching and tensioning with the tissue near the sacrum and/or tail bones.

As shown, the implant 600 has a Y-shaped configuration. The first elongate member 602 has a first end portion 601 and a second end portion 603 such that the first end portion 601 couples to or proximate to a portion of the vaginal wall, such as a posterior portion of the vaginal wall (or tissue proximate such wall) and the second end portion 603 coupled to or proximate to sacrum tissue of the patient. The second elongate member 604 also has a first end portion 605 and second end portion 607 such that the former couples to a portion of the vaginal wall, such as a portion of the anterior vaginal wall, and the latter couples to or proximate to sacrum tissue of the patient.

Implant 600 may be substantially similar to implants 200, 300, and 400 described with reference to FIGS. 2-4. Thus, similar to such implants, the implant 600 may be used to provide support to the vagina of the patient in case of vaginal vault prolapse.

Figure 10:
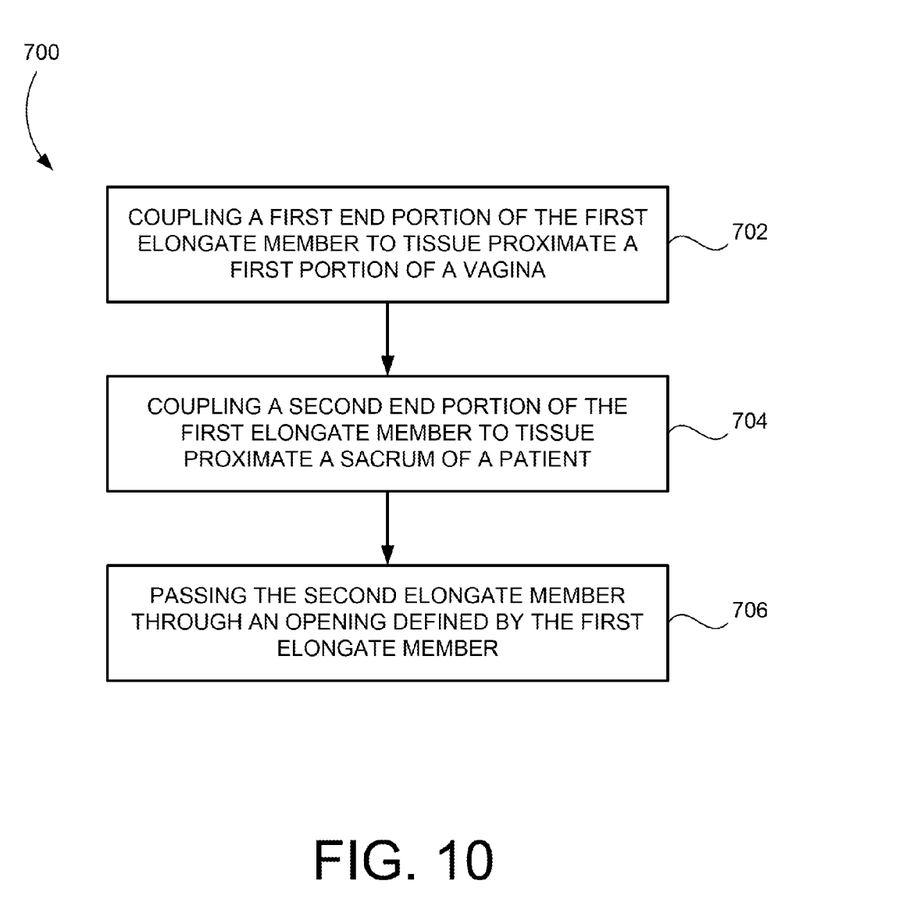
FIGS. 10 and 11 are flow charts of methods for placing an implant within a body of a patient, according to embodiments of the invention.

FIG. 10 is a flow chart illustrating one method 700 of placing an implant within a pelvic region of a patient. In one embodiment, the method 700 includes making an abdominal incision to insert the implant at a target location within the pelvic region of patient. The incision can be done using any suitable device such as knife, or the like. In some embodiments, the procedure may be performed laproscopically. Once the incision is done, the implant is positioned at the target location to fit the anatomy of the patient's body. More specifically, at step 702, the method includes coupling a first end portion of the first elongate member to tissue proximate a first portion of the vagina such as a posterior wall of the vagina (or tissue proximate such wall).

At step 704, the implant may then be positioned within the pelvic region of the patient such that a second end portion of the first elongate member is coupled to a sacrum (or tissue proximate the sacrum) of the patient. Before coupling, the physician may pull on the second end portion to apply tension to the first elongate member and choose the location of the coupling along the length of the first elongate member so as to apply sufficient tension and fit the anatomy of the patient's body. The two end portions of the first elongate member may be coupled to bodily tissue using mechanisms such as stitching, sewing, gluing, stapling, or the like.

At step 706, the second elongate member of the implant is passed through an opening defined in the first elongate member of the implant. The implant can be passed through the opening of first elongate member in any order such as before or after the steps 702 and/or 704. An end portion may then be coupled to a portion of the vaginal wall of the patient, such as the anterior portion of the vaginal wall (or tissue proximate the anterior portion of the vaginal wall). Appropriate tension may be applied to the second elongate member. Additionally, in some embodiments, the second elongate member may be coupled to the first elongate member, such as via a suture.

In the present method of placing the implant, the two elongate members can be tensioned independently by first fixing the first elongate member at both the vaginal tissue and the sacral tissue. Following that the second elongate member can be fed through the opening of the first elongate member (a shown in FIG. 5) and affixed to the vaginal and sacral tissue to hold or support the vaginal walls at both posterior and anterior ends.

Figure 11:
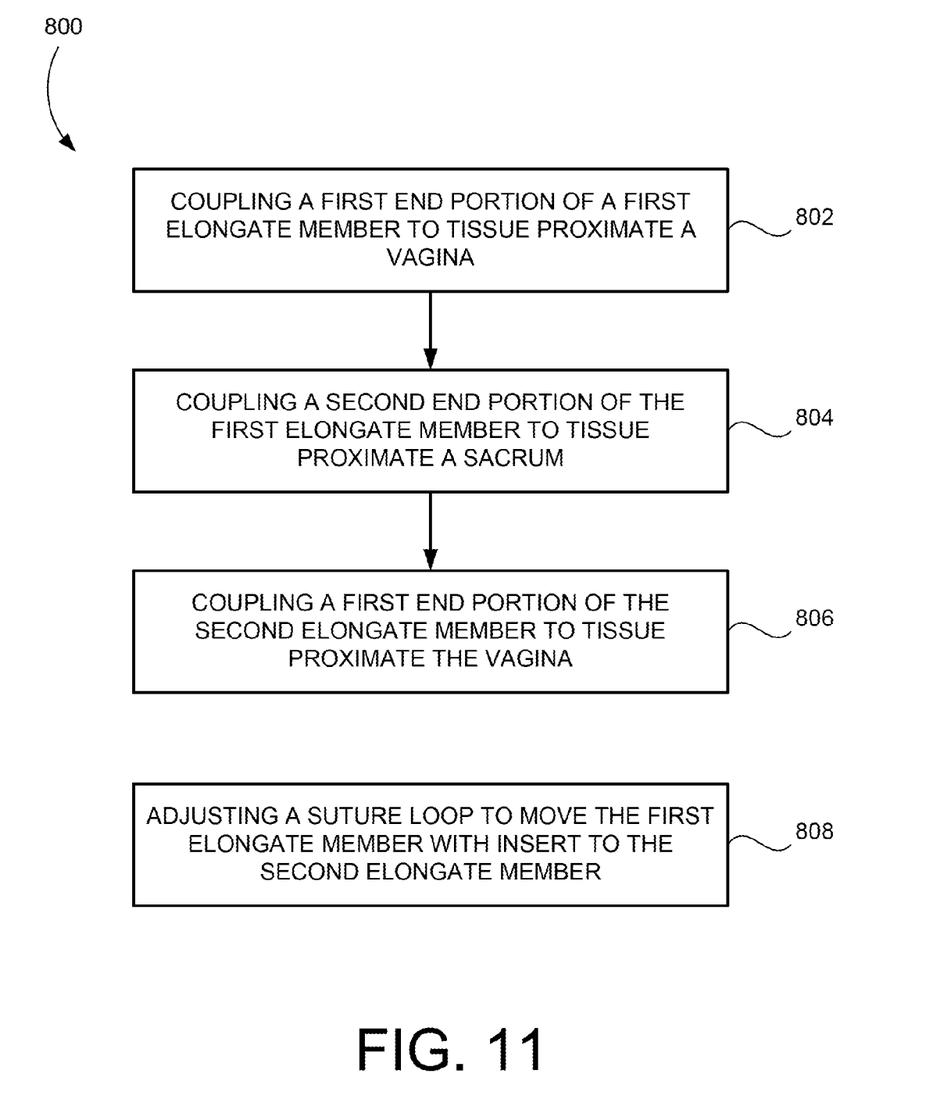

FIG. 11 is a flow chart illustrating another method 800 of placing an implant within a pelvic region of a patient. Similar to method 700 of FIG. 10, the method 800 includes making an abdominal incision to insert the implant at a target location within the pelvic region of patient. The incision can be done using any suitable device such as knife, or the like. Once the incision is done, the implant is positioned at the target location to fit the anatomy of the patient's body.

At step 802, the implant 800 a first end portion of the first elongate member is coupled to tissue proximate a first portion of the vagina, for example, where the first portion includes a posterior vaginal wall.

At step 804, the implant may then be positioned within the pelvic region of the patient such that a second end portion of the first elongate member is coupled to or proximate to a sacrum of the patient. In other embodiments, one end of the first elongate member may be coupled to or proximate to sacrum tissue and then another end may be coupled to or proximate to vaginal tissue. When one end is fixed, the physician may apply tension on the first elongate member as needed.

At step 806, first end portion of the second elongate member is coupled to a tissue proximate a second portion of the vagina, where the second portion includes an anterior vaginal wall.

At step 808, a suture loop may be adjusted to move the first elongate member with respect to the second elongate member. Such adjustments may include pulling or tying the first elongate member relative to the second elongate member. The adjustment of two elongate members creates a tension in the implant to support the vaginal apex of the patient, which employs coupling of the two elongate members at the vaginal wall and the sacrum of the patient. In some embodiments, the first elongate member and the second elongate member is coupled to bodily tissue using mechanisms such as stitching or sewing. For example, in some embodiments, the first end portion is coupled to or proximate to a posterior portion of the vaginal apex of the patient and the second end portion is coupled to a sacrum tissue such as sacrospinous ligament of the patient.

In some embodiments, an implant including a first elongate member having a first end portion and a second end portion, the first end portion of the first elongate member being configured to be coupled to tissue proximate a vagina of a patient, the second end portion of the first elongate member being configured to be coupled to tissue proximate a sacrum of the patient, the first elongate member defining a first opening and a second opening; and a second elongate member having a first end portion and a second end portion, the second elongate member configured to extend through the first opening and the second opening, the first end portion of the second elongate member being configured to be coupled to tissue proximate the vagina of the patient.

In some embodiments, the first elongate member is formed of a mesh material. In some embodiments, the first elongate member is formed of a mesh material having a plurality of fibers, the mesh material defining interstices between the fibers of the mesh materials, at least one of the interstices having a size, the first opening having a size, the size of the first opening being larger than the size of the at least one interstice. In some embodiments, the first elongate member is formed of a mesh material, and the second elongate member is formed of a mesh material.

In some embodiments, the second end portion of the first elongate member is coupled to the second end portion of the second elongate member. In some embodiments, the second end portion of the first elongate member is coupled to the second end portion of the second elongate member to form a loop portion. In some embodiments, the second end portion of the first elongate member is coupled to the second end portion of the second elongate member to form a loop portion, the second opening being disposed between the first opening and the loop portion.

In some embodiments, an implant includes a first elongate member having a first end portion and a second end portion, the first end portion of the first elongate member being configured to be coupled to tissue proximate a vagina of a patient, the second end portion of the elongate member being configured to be coupled to tissue proximate a sacrum of the patient, the first elongate member defining an opening; and a second elongate member having a first end portion and a second end portion, the second elongate member configured to extend through the opening, the first end portion of the second elongate member being configured to be coupled to tissue proximate the vagina of the patient, the second end portion of the second elongate member being configured to be coupled to tissue proximate the sacrum of the patient.

In some embodiments, the first elongate member is formed of a mesh material. In some embodiments, the first elongate member is formed of a mesh material having a plurality of fibers, the mesh material defining interstices between the fibers of the mesh materials, at least one of the interstices having a size, the opening having a size, the size of the opening being larger than the size of the at least one interstice. In some embodiments, the first elongate member is formed of a mesh material, the second elongate member is formed of a mesh material. In some embodiments, the first elongate member has a width, the second elongate member has a width, and the width of the first elongate member being greater than the second elongate member.

In some embodiments, an implant includes a first elongate member having a first end portion and a second end portion, the first end portion of the first elongate member being configured to be coupled to tissue proximate a vagina of a patient, the first elongate member having a coupling tab; and a second elongate member having a first end portion and a second end portion, the first end portion of the second elongate member being configured to be coupled to tissue proximate the vagina of the patient, the second end portion of the second elongate member being configured to be coupled to the coupling tab of the first elongate member.

In some embodiments, the second end portion of the second elongate member is coupled to the coupling tab of the first elongate member via a suture. In some embodiments, first elongate member includes a side portion, the coupling tab extending from a side portion of the first elongate member. In some embodiments, the coupling tab is a first coupling tab, the first elongate member includes a second coupling tab configured to be coupled to the second elongate member.

In some embodiments, a method of placing an implant, the implant having a first elongate member and a second elongate member, includes coupling a first end portion of the first elongate member of the implant to tissue proximate a first portion of a vagina of a patient; coupling a second end portion of the first elongate member of the implant to tissue proximate a sacrum of the patient; and passing the second elongate member through an opening defined by the first elongate member.

In some embodiments, the method further includes coupling a first end portion of the second elongate member to tissue proximate a second portion of the vagina of the patient. In some embodiments, the method further includes moving the second elongate member with respect to the first elongate member.

In some embodiments, the first elongate member defines a first opening and a second opening, the second elongate member extending through the first opening and through the second opening.

In some embodiments, a method of placing an implant, the implant having a first elongate member and a second elongate member, includes coupling a first end portion of the first elongate member of the implant to tissue proximate a first portion of a vagina of a patient; coupling a second end portion of the first elongate member of the implant to tissue proximate a sacrum of the patient; coupling a first end portion of the second elongate member to the first elongate member; and adjusting a suture loop to move the first elongate member with respect to the second elongate member.

In some embodiments, the suture loop extends through a coupling tab of the first elongate member.

In some embodiments, an implant includes an elongate member having a first end portion, a second end portion, and a middle portion disposed between the first end portion and the second end portion, the first end portion of the elongate member being configured to be coupled to tissue proximate a vagina of a patient, the second end portion of the elongate member being configured to be coupled to tissue proximate the vagina of the patient, the middle portion being configured to be coupled to tissue proximate a sacrum of the patient, the elongate member defining an opening, a portion of the elongate member being configured to extend through the opening.

In some embodiments, the opening is a first opening, the elongate member defining a second opening, the elongate member having a portion configured to extend through the second opening.

While the steps illustrated above may provide a method for placing implants within a patient's body, variations are also contemplated to these methods for achieving the same or a similar goal. It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one exemplary embodiment in other embodiments. The disclosure's scope is, of course, defined in the language in which the appended claims are expressed.

What is claimed is:

1. An implant, comprising:
a first elongate member having a first end portion and a second end portion, the first end portion of the first elongate member being configured to be coupled to tissue proximate a vagina of a patient, the second end portion of the first elongate member being configured to be coupled to tissue proximate a sacrum of the patient, the first elongate member defining a first opening and a second opening; and a second elongate member having a first end portion and a second end portion, the second elongate member configured to extend through the first opening and the second opening, the second end portion of the second elongate member being coupled to the second end portion of the first elongate member to form a loop portion, the first end portion of the second elongate member being configured to be coupled to tissue proximate the vagina of the patient.

2. The implant of claim 1, wherein the first elongate member is formed of a mesh material.

3. The implant of claim 1, wherein the first elongate member is formed of a mesh material having a plurality of fibers, the mesh material defining interstices between the fibers of the mesh materials, at least one of the interstices having a size, the first opening having a size, the size of the first opening being larger than the size of the at least one interstice.

4. The implant of claim 1, wherein the first elongate member is formed of a mesh material, and the second elongate member is formed of a mesh material.

5. The implant of claim 1, wherein the second opening is disposed between the first opening and the loop portion.

6. The implant of claim 1, wherein the first elongate member and the second elongate member are unitarily formed.

7. An implant, comprising:
a first elongate member having a first end portion and a second end portion, the first end portion of the first elongate member being configured to be coupled to tissue proximate a vagina of a patient, the second end portion of the first elongate member being configured to be coupled to tissue proximate a sacrum of the patient, the first elongate member defining a first opening and a second opening; and a second elongate member having a first end portion and a second end portion, the second elongate member extending through the first opening and the second opening, the first end portion of the second elongate member being configured to be coupled to tissue proximate the vagina of the patient, the second end portion of the second elongate member coupled to a middle portion of first elongate member.

8. The implant of claim 7, wherein the second elongate member is frictionally coupled to the first elongate member while extending through the first opening and the second opening.

9. The implant of claim 7, wherein the first elongate member is formed of a mesh material.

10. The implant of claim 7, wherein the first elongate member is formed of a mesh material having a plurality of fibers, the mesh material defining interstices between the fibers of the mesh materials, at least one of the interstices having a size, the first opening having a size, the size of the first opening being larger than the size of the at least one interstice.

11. The implant of claim 7, wherein the first elongate member is formed of a mesh material, the second elongate member is formed of a mesh material.

12. The implant of claim 7, wherein the first elongate member has a length longer than a length of the second elongate member.

* * * * *